United States Patent [19]

Johnson

[11] 3,976,650

[45] Aug. 24, 1976

[54] PROCESS FOR PREPARING OPTICALLY ACTIVE 6,7-DIMETHOXY-2-METHYL-4-OXO-1,2,3,4-TETRAHYDRO-1-QUINOLINE CARBOXYLIC ACID ESTER ANALGESICS

[75] Inventor: Michael R. Johnson, Gales Ferry, Conn.

[73] Assignee: Pfizer Inc., New York, N.Y.

[22] Filed: Nov. 4, 1975

[21] Appl. No.: 628,778

[52] U.S. Cl. .................... 260/287 K; 260/240 R; 260/471 A; 260/518 R; 424/258
[51] Int. Cl.$^2$ ..................................... C07D 215/12
[58] Field of Search ................... 260/287 K, 287

[56] References Cited

UNITED STATES PATENTS

| | | | |
|---|---|---|---|
| 2,421,693 | 6/1947 | Harriman | 260/287 |
| 3,347,856 | 10/1967 | Lunsford | 260/287 |
| 3,446,805 | 5/1969 | Wirth et al. | 260/287 K |
| 3,455,929 | 7/1969 | Belleau et al. | 260/287 |
| 3,637,846 | 1/1972 | Plostnieks | 260/287 K |

*Primary Examiner*—Nicholas S. Rizzo
*Assistant Examiner*—David E. Wheeler
*Attorney, Agent, or Firm*—Connolly and Hutz

[57] ABSTRACT

Process for preparing d(+)-6,7-dimethoxy-2-methyl-4-oxo-1,2,3,4-tetrahydro-1-quinoline carboxylic acid, alkyl or benzyl esters as analgesic agents.

5 Claims, No Drawings

PROCESS FOR PREPARING OPTICALLY ACTIVE 6,7-DIMETHOXY-2-METHYL-4-OXO-1,2,3,4-TETRAHYDRO-1-QUINOLINE CARBOXYLIC ACID ESTER ANALGESICS

BACKGROUND OF THE INVENTION

This invention relates to a process for the preparation of the dextrorotatory enantiomer of 6,7-dimethoxy-2-methyl-4-oxo-1,2,3,4-tetrahydro-1-quinoline carboxylic acid, alkyl and benzyl esters which are useful as analgesic agents in the treatment and control of pain.

SUMMARY OF THE INVENTION

This invention relates to a novel chemical process for the preparation of the dextrorotatory enantiomer of a compound of the formula

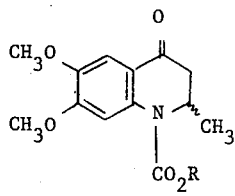

wherein R is alkyl of one to four carbon atoms or benzyl, said process comprising the consecutive steps of
1. contacting a racemic mixture of a compound of the formula

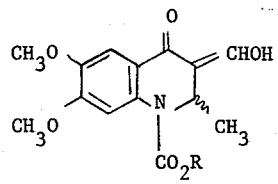

with an equivalent amount of d(+)-1-(1-naphthyl)ethylamine in a reaction-inert solvent,
2. separating the resulting pair of diastereomers,
3. contacting individually the separated diastereomers of the formula

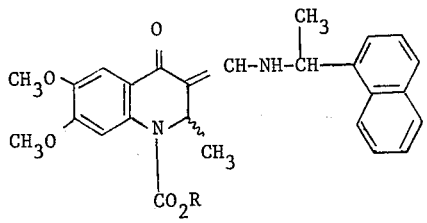

with at least one equivalent of ammonium acetate in an alkanol of one to three carbon atoms, and
4. hydrolyzing individually the resulting isomers of a compound of the formula

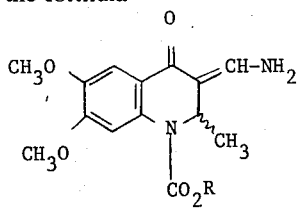

with one equivalent of an alkali metal or alkaline-earth metal hydroxide in an aqueous-alkanol solvent system, said alkanol of one to three carbon atoms.

A preferred feature of the claimed process is the use of benzene, the reaction-inert solvent in step 1), and ethanol as the alkanol in steps 3) and 4).

A further preferred feature of the claimed process is the separation of the pair of diastereomers by column chromatography on silica gel.

In addition to being useful as analgesic agents, the compounds of the claimed process are also tranquilizing agents.

Since the absolute configuration of the methyl substituent at the 2-position is not known, the bond of the methyl group to the 2-position is depicted as

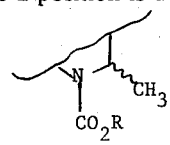

DETAILED DESCRIPTION OF THE INVENTION

In accordance with the process of the claimed invention, the following scheme is illustrative of the steps involved:

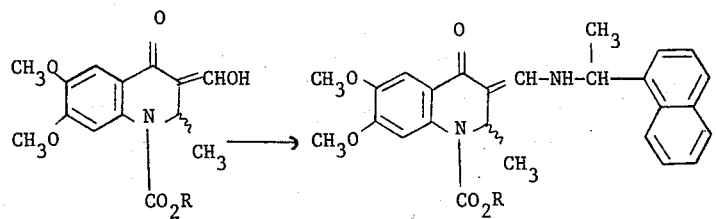

(mixture of diastereomers)

II ⟶ 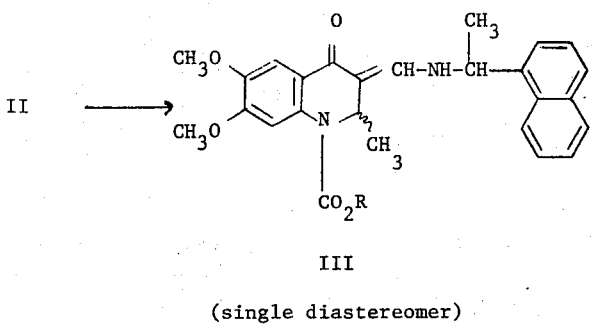

III
(single diastereomer)

III ⟶ 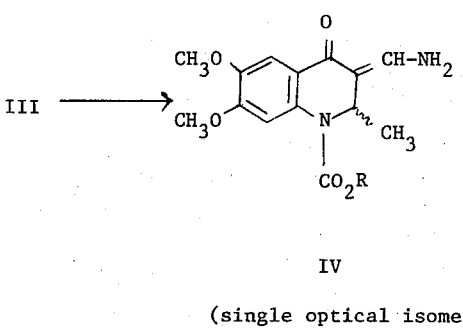

IV
(single optical isomer)

IV ⟶ 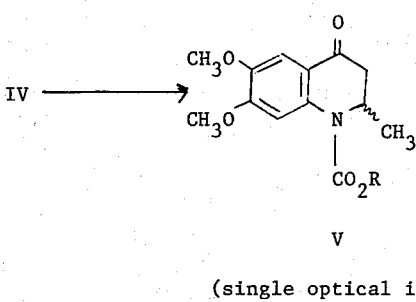

V
(single optical isomer)

wherein R is as previously defined.

In the first step of the above-depicted scheme, the hydroxymethylene compound of formula I is reacted with one of the optical isomers of an amine $NH_2$-Q which has an asymmetric center in the group Q. For the present invention it is preferred that $NH_2$-Q is d(+)-1-(1-naphlyl)ethylamine. It is further preferred that this reaction be carried out in a reaction-inert solvent, said solvent being one which solubilizes the reactants and does not react with either the starting materials or product to any appreciable extent. Such solvents include liquid aromatic hydrocarbons, liquid alkanols, chlorinated hydrocarbons and dialkyl and cyclic ethers. The preferred solvent is benzene.

Reaction time is not critical and is inherently dependent on the reactivity of the starting materials, concentration and reaction temperatures. When ambient temperatures are employed a reaction time of 12–24 hours may be required. When the reflux temperature of benzene is used, the reaction is complete in several hours.

In order to minimize cost and maximize the purity of the product, it is preferred that equimolar amounts of the reactants be employed. However, larger amounts of the amine $NH_2$-Q can be used without demonstrably changing the course of the reaction.

Isolation of the product is achieved by removal of the solvent and dissolution of the residue with chloroform. The chloroform is then washed with dilute base in order to remove any of the unreacted hydroxymethylene starting material. Drying and removal of the chloroform leaves the product as a mixture of two diastereomers.

The second step in the claimed sequence of reactions relates to the separation of the mixture of two diastereomers.

All the methods which are applicable for this purpose are well known to those skilled in the art, and include fractional crystallization, column chromatography, high-pressure chromatography and thin- or thick-layer chromatography. In the process of the present invention it is preferred that the mixture of the diastereomers be separated by column chromatography using silica gel as the adsorbant material and benzene acetonitrile (15:1 V:V) as the eluate. The less polar diastereomer is more mobile on the column leaving the more polar diastereomer closer to the point of application on the column. Detection of the diastereomers on the column is done in the usual manner using their capacity to absorb ultra-violet light as a marker.

When a glass column is employed, elution can be continued until the less polar diastereomer is carried off the column with the eluate, leaving the more polar diastereomer behind for further elution. If a nylon column or one of similar material is used, it may be cut into sections, said sections containing the separated diastereomers adsorbed to the column material. In the latter case the separated diastereomers are eluted from the adsorbant by a suitable solvent and the column material filtered. The filtrate is then concentrated to dryness leaving the single diastereomer.

Each diastereomer of formula III is converted to the corresponding 3-aminomethylene optical isomer by treatment with ammonium acetate in a suitable alcohol of one to three carbon atoms.

Although only one equivalent of ammonium acetate is required in this reaction, it is preferred that an excess as large as one-hundred fold be employed. This excess ensures completeness of reaction in a minimum reaction time.

Reaction time is not critical, and when the reaction is conducted at the reflux point of ethanol, the preferred alcohol, and with an excess of ammonium acetate the reaction is complete in 6–8 hours.

Isolation of the product is achieved by addition of the cooled reaction mixture to ethyl acetate followed by a water wash. The separated, dried organic phase is then concentrated to dryness and the residue purified by conventional means.

Hydrolysis of the individual isomeric 3-aminomethylene compounds of formula IV is achieved by treatment with base. In general, it is preferred that an organic base be employed, particularly an alkali metal or alkaline-earth metal hydroxide. In addition, because of the lability to hydrolysis of the ester group on the 1-position, it is preferred that one equivalent of said base be employed.

In order to facilitate hydrolysis, a water miscible alcohol is added to the aqueous solution of the aforementioned base. The presence of the alcohol increases the solubility of the requisite substrate to be hydrolyzed; the preferred alcohol is ethanol.

Reaction time is not critical and dependent on herein-before-discussed parameters. At the reflux temperature of the aqueous-alcohol solvent system the reaction is usually complete in 24–36 hours.

Removal of the solvent under reduced pressure followed by the partition of the residue between water-ethyl acetate provides, on evaporation of the ethyl acetate layer, the desired final single optical isomers. Further purification is effected by conventional means.

In some instances, the crude product from the hydrolysis of the aminomethylene compound of the formula IV is contaminated with the corresponding 6,7-dimethoxy-2-methyl-4-oxo-1,2,3,4-tetrahydroquinoline, i.e. the product in which the alkoxy- or benzyloxycarbonyl group has been removed from the nitrogen atom of the tetrahydroquinoline. When this occurs to a significant extent, it is convenient to treat the reaction product with the appropriate chloroformate of formula Cl-CO-OR, in the presence of a base, thereby increasing the ultimate yield of the optically active compound of formula V.

As will be recognized by one with skill in the art, the compounds represented by the formula V possess an asymmetric carbon atom, and therefore they can exist in two forms. These forms can be extinguished by their ability to rotate the plane of plane-polarized light. One form rotates the plane of polarized light to the right and is known as the dextrorotatory enantiomer or the d-enantiomer; the other form rotates the plane of polarized light to the left and is known as the levorotatory enantiomer or the $l$-enantiomer. A mixture of equal amounts of the d- and $l$-enantiomers of a compound of formula V does not affect the plane of plane-polarized light, and it is known as a racemic mixture of d$l$ form.

For the purposes of the present invention, when determining whether a compound is dextrorotatory or levorotatory, it is the effect of the compound on light having a wavelength of 5893 Angstroms (the so-called D line of sodium) which is to be considered. This is of importance, since it is the dextrorotatory form of the final product of the claimed process which possess the analgesic activity.

The starting 3-hydroxymethylene compound of formula I are prepared by the here-in-described procedures.

As previously mentioned, the dextrorotatory products of the present process are valuable analgesic agents. Particularly useful in this regard are those products wherein R is ethyl and benzyl. The present invention is restricted to the dextrorotatory enantiomer, since when the dextrorotatory and levorotatory enantiomers of 6,7-dimethoxy-2-methyl-4-oxo-1,2,3,4-tetrahydro-1-quinoline carboxylic acid, alkyl and benzyl esters were prepared and tested for analgesic activity, it was determined that while the dextrorotatory enantiomer shows analgesic activity, the levorotatory enantiomer does not demonstrate this utility.

The analgesic agents of the present invention are characterized by relief of pain in humans. Standard procedures of detecting and comparing analgesic activity of compounds in this series and for which there is an excellent correlation with human efficacy is the flinch-jump in rats test, as taught by W. Evans, Psychopharmacologia, 2, 318 (1961) and by S. Tenen, Psychopharmacologia, 12, 278 (1968).

The compounds of the present process, useful as analgesics, can be administered either as individual therapeutic agents or as mixtures of therapeutic agents. They may be administered alone, but are generally administered with a pharmaceutical carrier selected on the basis of the chosen route of administration and standard pharmaceutical practice. For example, they can be administered orally in the form of tablets or capsules containing such excipients as starch, milk sugar, or certain types of clay, etc. They can be administered in the form of elixirs or oral suspensions with the active ingredients combined with emulsifying and/or suspending agents. They may be injected parenterally, and for this use they, or appropriate derivatives, may be prepared in the form of sterile aqueous solutions. Such aqueous solutions should be suitably buffered, if necessary, and should contain other solutes such as saline or glucose to render them isotonic.

Although the use of the present invention is directed toward the treatment of mammals in general, the preferred subject is humans. In determining an efficacious dose for human therapy, results of animal testing are frequently extrapolated and a correlation is assumed between animal test behavior and proposed human dosage. When a commercially employed standard is available, the dose level of the clinical candidate in humans is frequently determined by comparison of its performance with the standard in an animal test. For example, if a standard analgesic agent is administered effectively to humans at the rate of 100 to 400 mg. daily, it is assumed, then, that if compounds of the present invention have activity comparable to this standard in the test assay, that similar doses will provide comparable responses in humans.

Obviously, the physician will ultimately determine the dosage which will be most suitable for a particular individual, and it will vary with age, weight and response of the particular patient, as well as with the nature and extent of the symptoms and the pharmacodynamic characteristics of the particular agent to be administered. Generally, small doses will be administered initially, with a gradual increase in the dosage until the optimum level is determined. It will often be found that when the composition is administered orally, larger quantities of the active ingredient will be required to produce the same level as produced by a smaller quantity administered parenterally.

Having full regard for the foregoing factors, it is considered that a daily dosage of the compounds of the instant invention in humans of approximately 25 to 1500 mg., with a preferred range of 50 to 500 mg., will relieve pain effectively. These values are illustrative, and there may, of course, be individual cases where higher or lower dose ranges are merited.

The following examples are provided solely for the purpose of illustration and are not to be construed as limitations of this invention, many variations of which are possible without departing from the spirit or scope thereof.

EXAMPLE I 6,7-Dimethoxy-2-methyl-4-oxo-1,2,3,4-tetrahydroquinoline

A. Ethyl-3-[(3,4-dimethoxy)anilino]-2-butenoate

4-Aminoveratrole (62.0 g.), ethyl acetoacetate (63.0 g.), benzene (375 ml.), and acetic acid (2.1 ml.) are combined and refluxed in a flask equipped with a Dean-Stark trap to remove water until thin layer chromatography indicated the reaction is complete. The solvent is removed under reduced pressure to give a dark oil which crystallized upon standing. Recrystallization from hexane gives 79.0 g. of a tan powder, m.p. 59°–60°; a second crop afforded 6.7 g., m.p. 54°–56°. A sample is recrystallized from ethanol/water to give an analytical sample, m.p. 57°–58°.

Anal. Calc'd. for $C_{14}H_{19}NO_4$: C, 63.38; H, 7.22; N, 5.28.

Found: C, 63.45; H, 7.06; N, 5.33.

B. Ethyl-3-[(3,4-dimethoxy)anilino]butanoate

A mixture of 30.0 g. of the product of Example 1-A (m.p. 59°–60°), and 2.0 g. of platinum oxide in 250 ml. of acetic acid is hyrogenated in a Paar shaker at 50 p.s.i.; reduction is complete in 1 hr. The mixture is filtered and concentrated under reduced pressure to give an amber oil which is dissolved in chloroform and washed with sodium bicarbonate solution and saturated sodium chloride. The organic layer is dried over magnesium sulfate and concentrated under reduced pressure to give 30.0 g. of an amber oil which is used in the next step without further purification. A sample of oil is converted to the hydrochloride salt, m.p. 137.5°–139°. An equivalent sample of the hydrochloride salt (m.p. 138°–139.5°) is analyzed.

Anal. Calc'd. for $C_{14}H_{21}NO_4 \cdot HCL$: C, 55.35; H, 7.30; N, 4.61.

Found: C, 55.73; H, 7.33; N, 4.33.

C. 3-[(3,4-Dimethoxy)anilino]butanoic Acid

A 54 g. sample of the unpurified ester product of Example 1-B is combined with 17.5 g. of sodium hydroxide, 550 ml. of methanol and 130 ml. of water, and refluxed for 1.5 hrs. The reaction mixture is cooled, concentrated under reduced pressure, diluted with water and neutralized with 6N hydrochloric acid to give an oily mixture which is extracted with chloroform. The combined organic extracts are dried over anhydrous magnesium sulfate and concentrated under reduced pressure to give 48 g. of an oily product. This material is used in the next step without further purification.

D.

6,7-Dimethoxy-2-methyl-4-oxo-1,2,3,4-tetrahydroquinoline

The crude acid of Example I-C (48 g.) and 500 g. of polyphosphoric acid are heated for 1 hr. on a steam bath with vigorous stirring, then poured onto 700 g. of ice and extracted with chloroform. The organic extracts are dried over anhydrous magnesium sulfate and concentrated under reduced pressure to give 26.4 g. of a yellow solid, m.p. 145°–48°. A small sample is sublimed at 110° (.05 mm) to give a pale yellow solid, m.p. 150°–151°.

Anal. Calc'd. for $C_{12}H_{15}O_3N$: C, 65.14; H, 6.83; N, 6.33.

Found: C, 65.18; H, 6.86; N, 6.25.

EXAMPLE 2

Ethyl 6,7-dimethoxy-2-methyl-4-oxo-1,2,3,4-tetrahydroquinoline-1-carboxylate

A mixture of 15 g. of the quinoline product of Example I-D, 95 g. of potassium carbonate, and 225 ml. of methylene chloride are stirred for 1 hr., then 14.7 g. of ethyl chloroformate in 20 ml. of methylene chloride is added dropwise and the suspension is allowed to stir for 72 hrs. at room temperature. Additional 7.3 g. portions of ethyl chloroformate are added after 24 and 48 hrs. and 47 g. of potassium carbonate is added after 48 hrs. The reaction mixture is quenched with water and extracted several times with methylene chloride. The combined organic extracts are washed with water, dried over magnesium sulfate and concentrated under reduced pressure to give an oil which solidifies upon standing; trituration with 5% ethyl acetate in hexane gives 17 g. of a solid, m.p. 112°–116°. This solid is chromatographed on Silica Gel, eluting with 1:1 ethyl acetate/hexane, and recrystallized from 1:1 ethyl acetate/hexane to give 13.9 g. of white crystals, m.p. 116.5°–18°.

Anal. Calc'd. for $C_{15}H_{19}NO_5$: C, 61.42; H, 6.53; N, 4.78.

Found: C, 61.37; H, 6.51; N, 4.78.

EXAMPLE 3

Methyl 6,7-dimethoxy-2-methyl-4-oxo-1,2,3,4-tetrahydroquinoline-1-carboxylate

A mixture of 1.2 g. (5.45 mmol) of the quinoline product of Example 1-D, 792 mg. (10.7 mmol) of dry pyridine and 5.5 ml. of methylene chloride are stirred and cooled by an ice-water bath while 758 mg. (8.02 mmol) of methyl chloroformate in 1 ml. of methylene chloride is added over a 10 min. period at a rate to maintain a 10°–15°C temperature. The ice bath is removed and the reaction allowed to stir at room temperature for 45 min. then poured onto 25 ml. of saturated sodium bicarbonate solution. The methylene chloride layer is separated and washed with 25 ml. saturated sodium bicarbonate solution and saturated sodium chloride solution, then dried over magnesium sulfate, and gravity filtered and evaporated to a yellow solid. The solid is triturated with 5 ml. anhydrous ether, filtered, and washed with minimum ether, then air dried to 1.1 g. of a yellow solid, m.p. 156°–158°C. This material is dissolved in 10 ml. of hot ethyl acetate, treated with 50 mg. Darco G60, filtered and crystallized by the addition of hexane to give 727 mg. of an off-white solid, m.p. 159°–160°C. after drying in vacuum at 100°C. (1mm) for 24 hrs.

Anal. Calc'd. for $C_{14}H_{17}O_5N$: C, 60.2; H, 6.1; N, 5.0.
Found: C, 60.3; H, 6.3; N, 5.3.

EXAMPLE 4

Butyl 6,7-dimethoxy-2-methyl-4-oxo-1,2,3,4-tetrahydroquinoline-1-carboxylate

To a cooled mixture of 1.15 g. (5.17 mmol) of the quinoline product of Example 1-D, 751 mg. (10.15 mmol) of dry pyridine and 5.5 ml. of methylene chloride stirred under a nitrogen atmosphere is added dropwise 1.03 g. (7.60 mmol) of butyl chloroformate in 1 ml. methylene chloride over 10 min. at a rate to maintain a 10°–15°C. temperature. After the addition is complete the bath is removed, the reaction stirred at room temperature for 45 min., and poured onto 25 ml. saturated sodium bicarbonate solution. The organic phase is collected and washed with 25 ml. of saturated sodium bicarbonate solution, 50 ml. saturated sodium chloride solution, dried over magnesium sulfate, then gravity filtered and evaporated to a viscous amber oil. Evaporative distillation at 110°C. (0.05 mm) gave 1.4 g. of a very viscous amber oil.

Anal. Calc'd. for $C_{17}H_{23}O_5N$: C, 63.5; H, 7.2; N, 4.4.
Found: C, 63.7; H, 7.2; N, 4.1.

EXAMPLE 5

Benzyl 6,7-dimethoxy-2-methyl-4-oxo-1,2,3,4-tetrahydroquinoline-1-carboxylate

To a solution of 10.0 g. (45.3 mmol) of the quinoline product of Example 1-D in 75 ml. of pyridine cooled to 0°C. is added over a 30 min. period 55 ml. of benzyl chloroformate. After 20 min. the reaction mixture was warmed on a steam bath during which time the reaction became exothermic. Heating at steam bath temperatures is continued for 30 min., and the mixture allowed to cool to room temperature. The resulting suspension is added to a mixture of 550 ml. chloroform/300 ml. water. The chloroform layer is separated, washed successively with 10% hydrochloric acid (3 × 300 ml.), saturated aqueous sodium bicarbonate (1 × 200 ml.) and brine (1 × 200 ml.), and dried over magnesium sulfate. The chloroform layer is concentrated to dryness and the residue crystallized from ethyl acetate-hexane, 14.0 g. Recrystallization from the same solvent system gave 11.4 g. of the desired product, m.p. 127.5°–129.5°C.

Anal. Calc'd. for $C_{20}H_{21}O_5N$: C, 67.6; H, 6.0; N, 3.9.
Found: C, 67.5; H, 6.0; N, 3.8.

EXAMPLE 6

3-Hydroxymethylene-6,7-dimethoxy-2-methyl-4-oxo-1,2,3,4-tetrahydro-1-quinoline carboxylic acid, methyl ester Methyl 6,7-dimethoxy-2-methyl-4-oxo-1,2,3,4-tetrahydroquinoline-1-carboxylate (13.8 g.) in 140 ml. of benzene containing 19 ml. of ethyl formate is added to sodium ethoxide freshly prepared from 4.8 g. of sodium hydride and 6 ml. of ethanol over a period of 45 min. After stirring at room temperature for 4 hrs. the reaction mixture is poured onto 250 ml. of ice-water. The aqueous layer is retained and the organic layer washed with 1N aqueous sodium hydroxide. The washings are combined with the aqueous extracts and backwashed with benzene. The aqueous layer is then made acid with 12N hydrochloric acid and extracted with chloroform. The organic phase is separated, dried over r magnesium sulfate and evaporated in vacuo to dryness. The residue is employed in subsequent reactions without further purification.

EXAMPLE 7

3-Hydroxymethylene-6,7-dimethoxy-2-methyl-4-oxo-1,2,3,4-tetrahydro-1-quinoline carboxylic acid, ethyl ester To sodium ethoxide freshly prepared from 4.8 g. of sodium hydride and 6.0 ml. of ethanol is added 14.7 g. of ethyl 6,7-dimethoxy-2-methyl-4-oxo-1,2,3,4-tetrahydroquinoline-1-carboxylate and 19.8 ml. of ethyl formate in 150 ml. of benzene over a 45 min. period. The reaction mixture, after stirring at room temperature for 3 hrs., is poured onto 250 ml. of ice water. The aqueous layer is retained and the organic layer extracted with 1N aqueous sodium hydroxide. The base extracted is combined with the separated aqueous and backwashed with benzene. The aqueous layer is then added to 250 ml. of 12N hydrochloric acid, resulting in the formation of a yellow oil. Crystallization of the oil from hexane gives 15.4 g. of the desired intermediate, m.p. 98°–101°C. Further recrystallization from the same solvent raises the melting point to 129°–130°C.

Anal. Calc'd. for $C_{16}H_{19}O_6N$: C, 59.8; H, 6.0; N, 4.4.
Found: C, 59.7; H, 5.9; N, 4.3.

EXAMPLE 8

3-Hydroxymethylene-6,7-dimethoxy-2-methyl-4-oxo-1,2,3,4-tetrahydro-1-quinoline carboxylic acid, butyl ester To sodium ethoxide freshly prepared from 4.8 g. of sodium hydride and 6.0 ml. of ethanol is added 16.0 g. of butyl 6,7-dimethoxy-2-methyl-4-oxo-1,2,3,4-tetrahydroquinoline-1-carboxylate and 19.8 ml. of ethyl formate in 150 ml. of benzene over a 30 min. period. The reaction mixture, after stirring at room temperature for 4 hrs., is poured onto 250 ml. of ice-water. The aqueous layer is retained and the organic layer extracted with 1N aqueous sodium hydroxide. The base extracted is combined with the separated aqueous and backwashed with benzene. The aqueous layer is then added to 250 ml. of 12N hydrochloric acid. The resulting yellow oil is extracted with chloroform and the chloroform layer dried over magnesium sulfate. The solvent is removed under reduced pressure and the residual product used in subsequent reactions without further purification.

EXAMPLE 9

3-Hydroxymethylene-6,7-dimethoxy-2-methyl-4-oxo-1,2,3,4-tetrahydro-1-quinoline carboxylic acid, benzyl ester Following the procedure of Examples 6–8, 9.5 g. of benzyl 6,7-dimethoxy-2-methyl-4-oxo-1,2,3,4-tetrahydroquinoline-1-carboxylate, 10.95 ml. of ethyl formate and sodium ethoxide prepared from 2.57 g. of sodium hydride and 3.23 ml. of ethanol in 120 ml. of benzene gave on work-up a yellow oil which on crystallization afforded 6.0 g. of crude product, m.p. 106°–110°C. The analytical same is recrystallized several times from methanol, m.p. 116°–118°C.

Anal. Calc'd. for $C_{21}H_{21}O_6N$: C, 65.8; H, 5.6; N, 3.7. Found: C, 65.4; H, 5.6; N, 3.7.

EXAMPLE 10 d(+) and l(−) 3-[N-(1-{1-Naphthyl}ethyl)aminomethylene]-6,7-dimethoxy-2-methyl-4-oxo-1,2,3,4-tetrahydro-1-quinoline carboxylic acid, ethyl ester A mixture of 6.4 g. of racemic 3-hydroxymethylene-6,7-dimethoxy-2-methyl-4-oxo-1,2,3,4-tetrahydro-1-quinoline carboxylic acid, ethyl ester from Example 7 and 3.2 g. of d-1-(1-naphthyl)ethylamine in 60 ml. of benzene are stirred at ambient temperature for 16 hrs. The solvent is removed by evaporation in vacuo, and the residue is redissolved in 250 ml. of chloroform. The chloroform solution is washed with 150 ml. of 1N sodium hydroxide, and then the dried organic phase is concentrated to dryness in vacuo. This affords 9.3 g. of 3-[N-(1-[1-naphthyl]ethyl)aminomethylene]-6,7-dimethoxy-2-methyl-4-oxo-1,2,3,4-tetrahydro-1-quinoline carboxylic acid, ethyl ester as a mixture of two diasteriomers, $[\alpha]_D^{25} = -364.17°$ (1% solution in $CHCl_3$).

A 2.0 g. aliquot of the above mixture of diasteriomers is dissolved in 30 ml. of chloroform, and to the resultant solution is added 20 g. of chromatographic grade silica gel. The chloroform is then removed by evaporation in vacuo, and the residue placed on top of a chromotographic column which has been prepared by placing 760 g. of silica gel in a 50 × 1.6 inches nylon tube. The column is eluted with 1,280 ml. of 15:1 benzene: acetonitrile, and then allowed to run dry. The column is cut into small pieces, approximately 1 inch long, and each piece is triturated with ethyl acetate. The silica gel is removed by filtration, and the ethyl acetate removed by evaporation in vacuo, giving 15 column fractions.

Fractions 1–5 are combined, giving 290 mg. of the more polar diasteriomer of the above diasteriomeric mixture. The diasteriomer has $[\alpha]_D^{25} = -247.1°$ (1% in $CHCl_3$).

Fractions 14 and 15 are combined, giving 250 mg. of the less polar diasteriomer of the above diasteriomeric mixture. It has $[\alpha]_D^{25} = -407.2°$ (1% in $CHCl_3$).

Fractions 6–13 are rechromotographed, to provide further quantities of each of the pure diasteriomers.

EXAMPLE 11 d(+)-3-Aminomethylene-6,7-dimethoxy-2-methyl-4-oxo-1,2,3,4-tetrahydro-1-quinoline carboxylic acid, ethyl ester To a solution of 2.06 g. of the more polar diasteriomer, prepared by reaction of racemic 3-hydroxymethylene-6,7-dimethoxy-2-methyl-4-oxo-1,2,3,4-tetrahydro-1-quinoline carboxylic acid, ethyl ester with d-1-(1-naphthyl)ethylamine (Example 10), in 40 ml. of ethanol, is added 50 g. of ammonium acetate, and the reaction mixture heated to reflux. After 20 min. reflux and after 45 min. reflux, additional 25 g. quantities of ammonium acetate are added. The reaction mixture is heated under reflux for a total of 6 hrs., and then cooled to 25°C. and poured onto 1,000 ml. of ethyl acetate. The ethyl acetate solution is washed successively with water and sodium bicarbonate, dried over magnesium sulfate ($MgSO_4$), and concentrated in vacuo to give 1.55 g. of crude product as a viscous oil. The crude product is purified by column chromotography using silica gel as absorbant and 6:4 benzene-ethyl acetate as eluant, followed by recrystallization from chloroform-hexane, giving 440 mg. of material, m.p. 70°–120°C. A further recrystallization gave 290 mg., m.p. 92°–95°C., $[\alpha]_D^{25} = +97.62$ (0.25% in $CHCl_3$).

Anal. Calc'd. for $C_{16}H_{20}N_2O_5$: C, 60.0; H, 6.3; N, 8.8. Found: C, 60.1; H, 6.5; N, 8.3.

A further 500 mg. of product m.p. 88°–90°C. is obtained from the recrystallization mother liquors, giving a total yield of 790 mg. (56%).

Similar results are obtained when methanol or i-propanol are employed in place of ethanol.

EXAMPLE 12 d(+)-6,7-Dimethoxy-2-methyl-4-oxo-1,2,3,4-tetrahydro-1-quinoline carboxylic acid, ethyl ester A mixture of 950 mg. of d(+)-3-aminomethylene-6,7-dimethoxy-2-methyl-4-oxo-1,2,3,4-tetrahydro-1-quinoline carboxylic acid, ethyl ester 2.96 ml. of 1N sodium hydroxide and 4 ml. of ethanol is heated under reflux for 24 hrs. and then stored at 25°C. for 3 days. The solvent is removed by evaporation in vacuo, and the residue dissolved in ethyl acetate. The ethyl acetate solution is washed with water and then concentrated to give 970 mg. of an oil. The oil is chromatographed on 40 g. of silica gel, using 6:4 benzene-ethyl acetate as solvent. The early fractions are combined and concentrated in vacuo to give 470 mg. of the title compound as an oil. The oil is recrystallized twice from ethyl acetate-petroleum ether to give 178 mg. (20% yield) of the desired product, m.p. 94°–95°C., $[\alpha]_D^{25} = +135.5°$ (0.2% in $CHCl_3$).

Anal. Calc'd. for $C_{15}H_{19}O_5N$: C, 61.4; H, 6.5; N, 4.8. Found: C, 61.5; H, 6.6; N, 4.6.

Similar results are obtained when potassium hydroxide, calcium hydroxide, lithium hydroxide or magnesium hydroxide are used in place of sodium hydroxide and methanol or n-propanol are substituted for ethanol.

EXAMPLE 13 l(−)-3-Aminomethylene-6,7-dimethoxy-2-methyl-4-oxo-1,2,3,4-tetrahydro-1-quinoline carboxylic acid, ethyl ester The less polar diasteriomer from the reaction of the racemic 3-hydroxymethylene-6,7-dimethoxy-2-methyl-4-oxo-1,2,3,4-tetrahydro-1-quinoline carboxylic acid, ethyl ester with d-1-(1-naphthyl)ethylamine (Example 10) is treated with ammonium acetate, according to the procedure of Example 11, to give 46% yield of the desired product, m.p. 92°–95°C., $[\alpha]_D^{25} = -91.52°$ (0.2% in $CHCl_3$).

Anal. Calc'd. for $C_{16}H_{20}N_2O_5$: C, 60.0; H, 6.3; N, 8.8. Found: C, 60.4; H, 6.5; N, 8.3.

EXAMPLE 14 l(−)-6,7-Dimethoxy-2-methyl-4-oxo-1,2,3,4-tetrahydro-1-quinoline carboxylic acid, ethyl ester A mixture of l(−)-3-aminomethylene-6,7-dimethoxy-2-methyl-4-oxo-1,2,3,4-tetrahydro-1-quinoline carboxylic acid, ethyl ester 1.78 ml. of 1N sodium hydroxide and 3 ml. of ethanol are heated under reflux for 24 hrs. and then stored at 25°C. for 3 days. The solvent is removed by evaporation in vacuo, and the residue dissolved in ethyl acetate. The ethyl acetate solution is washed with water and then concentrated to give 540 mg. of an oil. The oil is chromatographed using 30 g. of silica gel, and 6:4 benzene-ethyl acetate as solvent, giving 6 fractions. Fractions 1 and 2 are combined and recrystallized from ethyl acetate-hexane to give 49 mg. of the title product, m.p. 92°–93°C. Fractions 3–6 are combined to give 152 mg. of 6,7-dimethoxy-2-methyl-4-oxo-1,2,3,4-tetrahydroquinoline. This latter material is dissolved in 3 ml. of methylene chloride, and 3 ml. of pyridine followed by 0.5 ml. of ethyl chloroformate was added. After 20 min., the reaction mixture is diluted with an excess of methylene chloride and water. The organic phase is separated and washed successively with dilute hydrochloric acid, saturated sodium bicarbonate and brine. The methylene chloride solution is then dried, and evaporated in vacuo to give an oil. The oil is recrystallized from ethyl acetate-hexane to give 95 mg. of the title compound, m.p. 92°–93°C.

The two crops of the title compound, together with 45 mg. of equivalent material from an analogous experiment, are further recrystallized to give a sample of the title compound having m.p. 94°–95°C., $[\alpha]_D^{25} = -140.7°$.

Anal. Calc'd. for $C_{15}H_{19}NO_5$: C, 61.4; H, 6.5; N, 4.8. Found: C, 61.2; H, 6.4; N, 4.6.

EXAMPLE 15

Condensation of the appropriate racemic 3-hydroxymethylene-6,7-dimethoxy-2-methyl-4-oxo-1,2,3,4-tetrahydro-1-quinoline carboxylic acid, alkyl or benzyl ester with d-1-(1-naphthyl)ethylamine according to the procedure of Example 10 produces the following mixture of two diasteriomers:

3-[N-(1-{1-naphthyl}ethyl)aminomethylene]-6,7-dimethoxy-2-methyl-4-oxo-1,2,3,4-tetrahydro-1-quinoline, methyl ester;

3-[N-(1-{1-naphthyl}ethyl)aminomethylene]-6,7-dimethoxy-2-methyl-4-oxo-1,2,3,4-tetrahydro-1-quinoline, butyl ester; and 3-[N-(1-{1-naphthyl}ethyl)aminomethylene]-6,7-dimethoxy-2-methyl-4-oxo-1,2,3,4-tetrahydro-1-quinoline, benzyl ester.

Each of the above diasteriomeric mixtures is separated into the individual diasteriomers by chromatography.

EXAMPLE 16

Each of the single diasteriomers obtained after chromatography in Example 15 is treated with ammonium acetate according to the procedure of Example 11, followed by hydrolysis according to the procedure of Example 12, to produce the following compounds in both the dextrorotatory and the levorotatory form:

6,7-dimethoxy-2-methyl-4-oxo-1,2,3,4-tetrahydro-1-quinoline carboxylic acid, methyl ester;

6,7-dimethoxy-2-methyl-4-oxo-1,2,3,4-tetrahydro-1-quinoline carboxylic acid, butyl ester; and 6,7-dimethoxy-2-methyl-4-oxo-1,2,3,4-tetrahydro-1-quinoline carboxylic acid, benzyl ester.

EXAMPLE 17

The analgesics prepared by the process of the present invention are evaluated by the aforementioned Flinch Jump Test which is a modification of the Evans, Psychopharmacologia, 2, 318 (1961), flinch jump procedure and comprises measuring "pain thresolds." The procedure involves placing Sprague-Dawley rats weighing 210–270 g. in a chamber and presenting them with a series of 1 sec. foot shocks in increasing intensity of 0.1, 0.2, 0.3, 0.4, 0.6, 0.8; 1.2 etc. (in milliamps). The shocks are presented at 30 sec. intervals at 0.5 and 2.0 hrs. after i.p. administration of the drug at a dose of 56 mg./kg., and the animal behavior is rated at the point at which the animals jump.

The following results exemplify this activity for dl, l and d forms of the indicated compound as measured in the Flinch Jump Test:

| Compound | Jump Threshold 56 mpk | |
|---|---|---|
| | 0.5 hr. | 2 hrs. |
| d(+)-6,7-dimethoxy-2-methyl-4-oxo-1,2,3,4-tetrahydro-1-quinoline carboxylic acid, ethyl ester | 1.51 | 1.45 |
| l(−)-6,7-dimethoxy-2-methyl-4-oxo-1,2,3,4,-tetrahydro-1-quinoline carboxylic acid, ethyl ester | 1.05 | 0.86 |
| d,l-6,7-dimethoxy-2-methyl-4-oxo-1,2,3,4-tetrahydro-1-quinoline carboxylic acid, ethyl ester | 1.58 | 1.45 |
| saline solution | 0.78 | 0.92 |

What is claimed is:

1. A process for the preparation of the dextrorotatory enantiomer of a compound of the formula

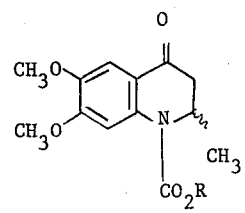

wherein R is selected from the group consisting of alkyl having one to four carbon atoms and benzyl, which comprises the consecutive steps of 1. contacting a racemic mixture of a compound of the formula

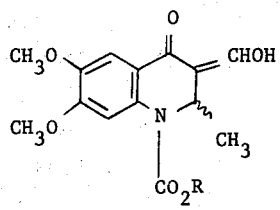

with an equivalent amount of dextrorotatory 1-(1-naphthyl)ethylamine in a reaction-inert solvent,
2. separating the resulting pair of diasteriomers,
3. contacting individually the separated diasteriomers of the formula

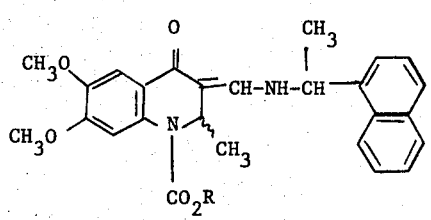

with at least one equivalent of ammonium acetate in an alkanol having one to three carbon atoms, and
4. hydrolyzing individually the resulting isomers of a compound of the formula

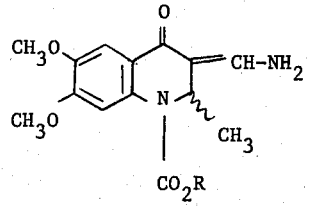

with one equivalent of a alkali metal of alkaline-earth metal hydroxide in an aqueous-alkanol solvent system, said alkanol having from one to three carbon atoms.

2. The process of claim 1 wherein the inert solvent of step 1 is benzene and the alkanol of steps 3 and 4 is ethanol.

3. The process of claim 2 wherein the pair of diasteriomers are separated by column chromatography on silica gel.

4. The process of claim 3 wherein R is ethyl.

5. The process of claim 3 wherein R is benzyl.

* * * * *